United States Patent [19]
Day et al.

[11] Patent Number: 4,732,854
[45] Date of Patent: Mar. 22, 1988

[54] METHOD OF PRODUCING DEXTRANASE

[75] Inventors: Donal F. Day; David W. Koenig, both of Baton Rouge, La.

[73] Assignee: Louisiana State University and Agricultural and Mechanical College, Baton Rouge, La.

[21] Appl. No.: 943,328

[22] Filed: Dec. 19, 1986

Related U.S. Application Data

[63] Continuation-in-part of Ser. No. 837,839, Mar. 10, 1986.

[51] Int. Cl.$^4$ .................. C12N 9/46; C12N 15/00; C12N 1/16; C12R 1/645
[52] U.S. Cl. .................. 435/211; 435/172.1; 435/255; 435/911
[58] Field of Search .................. 435/211, 255

[56] References Cited
U.S. PATENT DOCUMENTS 3,875,009 4/1975 Glasziou et al. .................. 435/211
3,912,594 10/1975 Shimada et al. .................. 435/211

OTHER PUBLICATIONS

Kreger-Van Rij, ed., The Yeasts, pp. 47, 48, 259, 260, (1984).
Webb et al. in Canadian Journal of Microbiology, vol. 29, pp. 1092–1095, (1983).
Laires et al. in Zeitschrift für Allgemeine Mikrobiologie, vol. 23(9), 601–603, (1983).

Primary Examiner—Lionel M. Shapiro
Attorney, Agent, or Firm—James M. Pelton

[57] ABSTRACT

A mutant species of *Lipomyces starkeyi* ATCC No. 12659 capable of hyperproducing dextranase and an improved method of culturing to achieve such at low pH to provide biologically contaminant free supernatant liquid containing dextranase. The further improved method of culturing the mutant species on a non-dextran, assimilable carbon source with optimal dextran induction is also disclosed.

17 Claims, 3 Drawing Figures

METHOD OF PRODUCING DEXTRANASE

CROSS-REFERENCE TO RELATED APPLICATION

This application is a continuation-in-part of application Ser. No. 837,839, filed Mar. 10, 1986, which is co-pending herewith.

BACKGROUND OF THE INVENTION

This invention relates to an improved method for producing dextranase, an enzyme capable of degrading dextran. More particularly this invention relates to an improved method which provides a dextranase product essentially free of biological contaminants. Further, this invention provides a novel culture of a mutant microorganism capable of hyperproducing dextranase.

Dextranase is used to hydrolyze dextran found in cane sugar production allowing the processing of previously unusable sugar juice for the production of sucrose. Dextranase has also been employed for the production of a dextran product which has found use as a blood substitute or extender. Because of its ability to hydrolyze dextran, dextranase has also been found highly useful for hydrolyzing the dextran produced by action of microorganisms causing dental caries or tooth decay. Thus, the incorporation of dextranase into a tooth powder, toothpaste or other oral detergent is considered in the art to provide a preventative or curative for tooth decay.

There are many known microorganisms capable of producing dextranase including moulds, e.g. fungi belonging to the genera Penicillium, Aspergillus, Spicaria, Fusarium and Chaetomium; bacteria, e.g. Lactobacillus, Cellvibrio, Flavobacterium and the like, see for example, U.S. Flavobacterium and the like, see for example, U.S. Pat. Nos. 2,742,399; 3,663,371; 3,875,009; and 3,912,594. In addition, it has also been reported that certain strains of yeasts have activity for dextranase, particularly strains of *Lipomyces starkeyi*, Webb and Spencer-Martins, Canadian Journal of Microbiology, Vol. 29, pages 1092-1095, 1983. However, this yeast has not been considered for industrial production of dextranase because of the reported slow growth of the organism and difficulty of avoiding contamination from other microorganisms during growth. This organism appears to be essentially acceptable under FDA procedures and, hence, useful in food industry dextranase applications.

In view of this, an object of the present invention is a method for culturing Lipomyces under unique conditions favoring rapid growth and low possibility of contamination by other microorganisms. Another object of this invention is a method for producing dextranase under conditions indicated by the prior art to be unproductive on an industrial scale. A further object of this invention is a dextranase product which is produced under conditions essentially free from biological contamination. These and other objects will be more fully illustrated in the following description of the invention. A still further object is the discovery and provision of a novel culture of a Lipomyces mutant capable of hyperproducing dextranase under the conditions found favorable for industrial scale production and without biological contamination.

THE INVENTION

This invention is based on the discovery and selection of a mutant species of the yeast *Lipomyces starkeyi* ATCC No. 12659, identified hereafter as Mutant I, which has been found to hyperproduce dextranase under certain conditions. As a result of such discovery and selection, there is provided a novel culture of the Mutant I capable of hyperproducing extracellular dextranase when cultured at a pH in the range of about 2.5 to about 4.5 in an aqueous nutrient medium containing an assimilable carbon source, a nitrogen source and a mineral source. A further aspect of the present invention features a method for producing extracellular dextranase which is improved over the above-identified parent application and which comprises culturing a mutant strain of the yeast *Lipomyces starkeyi* ATCC No. 12659 caused by ultraviolet light irradiation and characterized by hyperproduction of dextranase at a pH in the range of abut 2.5 to about 4.5 and in the presence of an aqueous nutrient medium, and then separating the vegetative cells to produce a dextranase-containing culture supernate. It is an additional discovery and feature of the above disclosed improved method for producing extracellular dextranase that the mutant species provided in the culture of this invention can be cultured using a non-dextran, assimilable carbon source and adding a dextran inducer at a stage of growth identified as having an adjusted optical density of from about 8.0 to about 10.0 at 660 nm compared with water. For example, when glucose is the assimilable carbon source, it has been found that the incremental addition of dextran at about 0.05 to about 0.2 weight percent of dextran per unit volume of aqueous culture medium advantageously induces the production of increased amounts of dextranase.

DESCRIPTION OF THE DRAWINGS

The method of the present invention will be more fully understood by reference to the figures of the accompanying drawings in which.

DESCRIPTION OF PREFERRED EMBODIMENTS OF THE INVENTION

Figure 1:
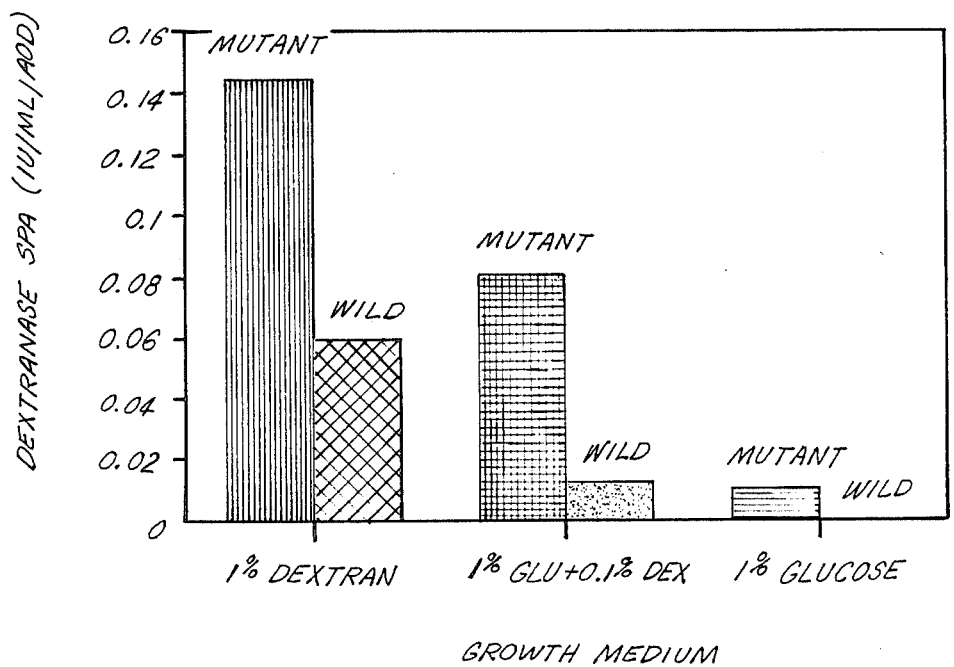
FIG. 1 is a bar graph representation of dextranase production after 72 hours comparing wild type *Lipomyces starkeyi* ATCC No. 12659 with Mutant I on various growth media.

Although some strains of Lipomyces have been known to produce dextranase, it has been found that *Lipomyces starkeyi* ATCC 12659 has a reduced lag time and grows well at lower pH and preferably in the highly acid pH range; more preferably between about pH 2.5-4.5. This feature of the invention provides industrial acceptability because of the essentially contamination-free production in this pH range. As used herein, the terms "contamination-free" or "biologically contamination free" mean that the conditions are much more favorable for growth of the Lipomyces than for other microorganisms; thus, at an acid pH range, most preferably of pH 2.5–4.5 very few microorganisms propagate at a rate sufficient to attain a concentration great enough to cause contamination problems.

Although the invention is not limited to this particular strain, a preferred strain, *Lipomyces starkeyi* ATCC No. 12659, was first identified from soil by R. L. Starkey, Journal of Bacteriology, Vol. 51, page 33 (1946). It was generally described by Lodder and Kreger-Van Rij in 1952, see H. J. Phaff and C. P. Kurtzman, *The Yeasts: A Taxonomic Study*, Ed. N. J. W. Kreger-Van Rij, 1984, Elsevier Publishers, Amsterdam, pages 259–260, which description is hereby incorporated by reference as if fully set forth. The yeast strain also has identification from other depositories, viz. NRRL Y-1389 and CB-1807 (Starkey's strain 74). In addition, other strains are known from the ATCC catalog and from previous publications, see Webb and Spencer-Martins, supra.

As a preferred embodiment of the present invention, a mutant of *Lipomyces starkeyi* ATCC No. 12659 was derived from the parent strain by ultraviolet light mutagenesis with subsequent selection on 2-deoxyglucose medium according to the procedure described in Laires et al, Journal of General Microbiology, Vol. 23, No. 9, 1983, pages 601–603, which is incorporated by reference as if fully set forth. This mutant, identified by the Letter "I" from its selection experiment (hereafter "Mutant I"), was selected based on its phenotypic stability for the derepressed trait, i.e., hyperproductivity of dextranase. No attempt was made to quantify the amount of reversion of Mutant I to the repressed trait. Except for the unexpected capability to hyperproduce dextranase under certain conditions, the taxonomic description of Mutant I is not discernibly different from the parent strain. A deposit of a sample of Mutant I has been made for purposes of this application with the American Type Culture Collection and has been assigned the number ATCC No. 20825. This deposit will be made permanently available, i.e., for thirty years or five years after the last request, whichever is later, to the public without restriction upon issuance of this application as a U.S. patent.

According to the present invention, Mutant I is cultured in a medium containing dextran, glucose or other assimilable carbon sources or mixtures thereof and a source of simple salts for about 2 to about 4 days. At the end of the culture period the vegetative cells may be separated and the culture medium may be used as a source of dextranase, e.g. such as, in processes directed to hydrolyze dextran.

In carrying out the method of this invention, an aqueous nutrient fermentation medium is inoculated with a growing culture of the Mutant I and the culture is then incubated under aerated conditions at a suitable temperature and pH. Typically the temperature is selected within the range of about 25° to about 30° C. Preferably, the temperature is controlled at about 27° C. and maintained at that temperature. The pH is controlled in an acid range preferably from about 3.0 to about 4.0.

The fermentation according to the present invention is carried out in a commercially available fermentation vessel. The culture medium is an aerated aqueous nutrient medium conventionally available, containing a source of assimilable carbon for growth and energy which preferably is also a suitable dextranase inducer and, more preferably, is dextran. Conventional minerals may also be added. A source of nitrogen is required for the production of dextranase. Preferably, a growth medium known as WW-DEX is used which contains the following:

| Reagent | Grams/Liter |
|---|---|
| Dextran (40,000 mol. wt.) | 10 |
| Potassium Phosphate, Monobasic | 2.5 |
| Ammonium Sulfate | 5.0 |
| Calcium Chloride | 0.1 |
| Sodium Chloride | 0.1 |
| Magnesium Sulfate | 0.1 |

The pH is adjusted with either HCl or NaOH, after sterilization, 1.0 ml of trace metals per liter are added. The trace metal stock has preferably the following composition:

| Reagent | Milligrams/Liter |
|---|---|
| Ferric Ammonium Sulfate | 14.00 |
| Zinc Sulfate Dihydrate | 3.00 |
| Manganese (II) Sulfate Tetrahydrate | 2.00 |
| Copper (II) Sulfate Pentahydrate | 0.30 |
| Ammonium Permolybdate | 0.09 |
| Boric Acid | 0.57 |

The trace metal stock is filter sterilized with a 0.2 micrometer filter.

It will be understood that the components of the nutrient medium can varied within known conventional limits and that the concentrations in which they are present can similarly be varied. Similarly, there can be supplemental additions or substitutions of any one of or a mixture of, for example, sugars such as sucrose, glucose and fructose and such variations together with variations in the mineral composition of the simple salts of the exemplified medium are well known in the art and are not further elaborated.

To provide oxygen for growth of the organism, the culture medium should be aerated during the incubation period. This can be achieved conveniently with the conventionally used aeration rate of between 0.25 and 1 liter of air per minute per liter of medium.

Suitably at least when using fermentation tanks the dissolved oxygen level can be monitored by means of a dissolved oxygen meter and the meter can be used to control the aeration rate as required by initiating a change in the degree of stirring of the medium or a change in the rate of air flow through the medium. Should either of these methods of aeration control lead to the production of excessive foam the situation can be rectified by the use of a mechanical foam breaker or, alternatively, the foam can be suppressed by addition of a conventional anti-foaming agent. When measurements indicate that a maximum concentration of dextranase has been reached in the culture medium the aeration and stirring are stopped. Since the dextranase is secreted by the organism it accumulates in and is conveniently recoverable in the supernatant liquid obtained by settling the cells and decanting the supernatant culture medium. This supernatant liquid may then be concentrated by other means, for example, it can be concentrated by salting out with ammonium sulfate, alcohol precipitation or applying reverse osmosis, ultrafiltration, phase extraction or ion exchange techniques.

The activity of a particular enzyme, specifically dextranase, is analyzed or assayed for potency by reducing sugar production by the method of Nelson-Somogyi, see Journal of Biological Chemistry, vol. 160, p. 61 (1945). This method is carried out by incubating a 0.2 ml sample of the clarified culture supernate liquid with 0.6 ml deionized water, 1.0 ml of 2 percent T-2000 dextran (obtained from Pharmacia Company, Ltd., Uppsala, Sweden) and 0.05 molar citrate phosphate at pH 5.5 and at 50° C. Then 0.5 ml of this mixture is assayed at various time intervals for the reducing sugar content. A unit of dextranase activity (IU) is defined as the amount of enzyme which liberates 1.0 micro mole of glucose equivalents per minute at the conditions described hereinabove.

It has also been found that the cells produced during the growth phase of the fermentation for the production of dextranase contained significant amounts of alpha-glucosidase. Thus, an additional feature of this invention is the co-production with dextranase of alpha-glucosidase which can be recovered from the washed cells according to known procedures. Some alpha-glucosidases are useful in starch conversion technology for production of sweeteners and alcohol, as an energy fuel or fuel additive. Alpha-glucosidase is assayed by collecting a known volume of culture supernate, removing the cells and concentrating or diluting with 0.1 molar phosphate buffer at pH 6.5. A sample of 0.8 milliliter is incubated at 30° C. and pH 6.6 with 0.1 ml of 40 mg/ml of para-nitrophenyl-alpha-glucopyranoside from Sigma Chemical Company in 0.1 molar potassium phosphate buffer at pH 8. At predetermined time intervals 0.1 ml of 3.0 molar sodium carbonate is added to stop the reaction and develop the color. The suspension is clarified and the amount of nitrophenol liberated is measured at 420 nm by spectrophotometer. A unit of alpha-glucosidase is defined as the amount of enzyme required to liberate one micro mole of nitrophenol per minute under the conditions described above.

Alpha-glucosidase is co-produced by the dextranase producing strain of *Lipomyces starkeyi* ATCC 12659. The conditions for optimum production of alpha-glucosidase are the same as those for production of the dextranase. Accordingly, the optimization of the dextranase producing properties of this yeast strain will also optimize alpha-glucosidase production.

As a further feature of the present invention, it has been discovered that the production of extracellular dextranase using an assimilable carbon source other than dextran or a dextran-like carbon source, that is, a non-dextran, assimilable carbon source, is markedly enhanced by the addition to the culture medium of a small amount of an inducer under certain conditions. Thus, the Mutant I species is shown to produce dextranase and have increased specific activity when small amounts of dextranase inducers are added to a culture medium in which the primary assimilable carbon source is a non-dextran, assimilable carbon source, preferably a carbohydrate selected from glucose, fructose, sucrose, and the like, or a carbohydrate containing material such as corn-steep liquor or molasses. The amount of inducer to be added to the non-dextran, assimilable carbon source containing culture medium can be from about 0.05 to about 0.2 percent by weight per unit volume of culture medium. More preferably, the amount of inducer is from about 0.1 to about 0.2 percent by weight per unit volume of culture medium. Typical and preferred inducers for dextranase are dextran, isomaltose and isomaltotriose, with dextran being more preferred. The non-dextran, assimilable carbon source can advantageously be selected from a number of conventional carbohydrates and nutrient solutions thereof, which are a less expensive assimilable carbon source than dextran. Thus, the use of a preferred dextranase inducer, such as dextran, in small amounts provides a cost effective method for dextranase production.

Having described the method of this invention in general, the following Examples will serve to further illustrate the invention and describe the best mode known to the inventors for carrying out the invention.

EXAMPLE 1

A culture of *Lipomyces starkeyi* ATCC No. 12659, and Mutant I, grown and maintained on the foregoing WW-DEX medium with 0.05 percent by weight per unit volume of 2-deoxyglucose, according to the procedure of Laires et al, supra, were transferred as 10 microliter inocula to 30 mm×150 mm cotton plugged test tubes containing 10 ml of media described as follows. The yeasts were grown on WW media including 1 percent by weight dextran, 1 percent by weight glucose plus 0.1 weight percent dextran, and 1 percent by weight glucose per unit volume, respectively. The aeration rate was 0.01 liters/min. with shaking at the rate of 200 rpm, and the temperature was maintained at 27° C. The result of dextranase production for all runs comparing the Wild and Mutant species is shown in Table I below.

TABLE I

DEXTRANASE ACTIVITY FROM *LIPOMYCES STARKEYI* ATCC NO. 12659 AND MUTANT I

Dextran Activity After 72 Hours

| Carbon sources* Culture | Activity (IU/ml) | | | Specific Activity (IU/AOD)** | | |
|---|---|---|---|---|---|---|
| | WW-DEX | WW-DG | WW-GLU | WW-DEX | WW-DG | WW-GLU |
| WILD | 0.741 | 0.061 | 0.000 | 0.060 | 0.013 | 0.000 |
| Mutant I | 2.126 | 0.588 | 0.072 | 0.145 | 0.082 | 0.011 |

*WW-DEX medium is WW medium with 1% w/v dextran.
WW-DG medium is WW medium with 1% w/v glucose and 0.1% w/v dextran.
WW-GLU medium is WW medium with 1% w/v glucose.
**AOD is Adjusted Optical Density and 1 AOD = $1.3 \times 10^6$ cells per ml FIG. 1 shows the results above in graphical form for the specific activity.

The best inducer for Mutant I grown on a non-dextran, assimilable carbon source, such as glucose, is selected based on the results of induction tests compared with dextran added at the beginning of the experiment as shown in Example 2 below.

EXAMPLE 2

Figure 2:
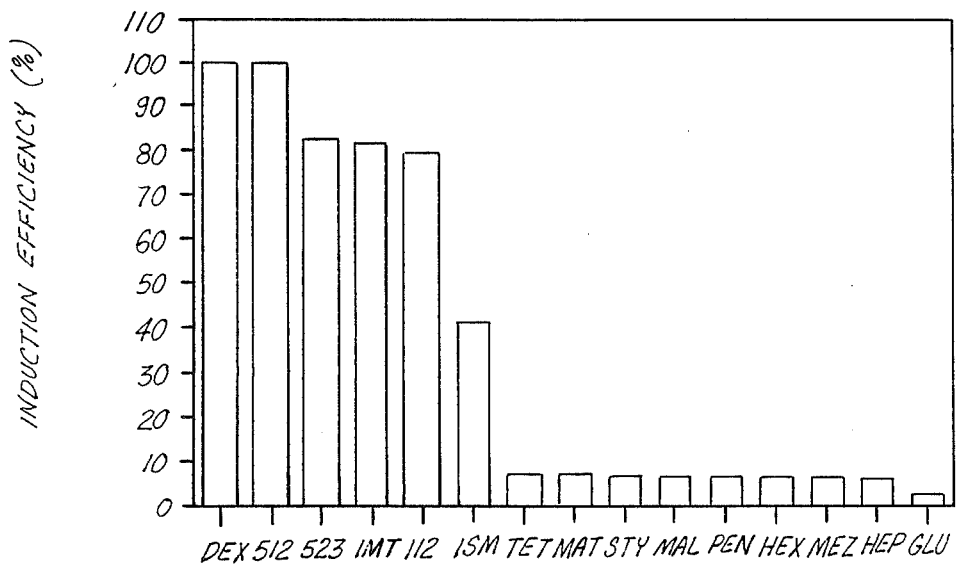
FIG. 2 is a bar graph representing the growth of Mutant I species on glucose and various inducer substrates and compared with a dextran induced control.

In a 30×150 mm cotton stoppered test tube containing 10 ml of media and sparged with air, was added an inoculum of Mutant I grown on a medium of WW-GLU (WW medium with 1 percent by weight glucose per unit volume) then concentrating and washing the cells in WW-medium without a carbohydrate source. The final volume of 5 ml was placed in the test tube together with 0.1 percent by weight of the proposed inducer per unit volume and 0.1 percent by weight of glucose per unit volume. After incubation for 5 hours at 27° C., the amount of dextranase was determined by assay and compared with the amount produced in a dextran-induced control. The results for several experiments are shown in Table 2 and FIG. 2 which graphically portrays the result.

TABLE 2

DEXTRANASE INDUCTION OF DEREGULATED MUTANT I

| Carbohydrate | Identification | % Induction |
|---|---|---|
| Dextran-Sigma | DEX | 100.0 |
| Dextran-Leuconostoc Strain 512 | 512 | 100.1 |
| Dextran-Leuconostoc Strain 523 | 523 | 82.7 |
| Isomaltotriose-Sigma | IMT | 81.9 |
| Dextran-Leuconostoc Strain 1120 | 112 | 79.6 |
| Isomaltose-Sigma | ISM | 41.3 |
| Maltotetrose-Sigma | TET | 7.5 |
| Maltotriose-Sigma | MAT | 7.3 |
| Stachyose-Sigma | STY | 7.0 |
| Maltose-Sigma | MAL | 6.8 |
| Maltopentose-Sigma | PEN | 6.7 |
| Maltohexose-Sigma | HEX | 6.5 |
| Melezitose-Sigma | MEZ | 6.4 |
| Maltoheptose-Sigma | HEP | 5.6 |
| Glucose-Sigma | GLU | 2.5 |
| Melibiose-Sigma | MEB | 2.6 |
| Panose-Sigma | PAN | 2.6 |
| Starch-Fisher | STR | 1.1 |
| Cellobiose-Sigma | CEL | 0.8 |
| Sorbose-Sigma | SRB | 1.7 |
| Melibiose-Sigma | MEB | 1.7 |
| Inulin-Sigma | INU | 0.2 |
| Amylose-Sigma | AMY | 0 |
| Dextrin-Fisher | RIN | 0 |
| Citrate-Sigma | CIT | 0 |
| Acetate-Sigma | ACE | 0 |
| Mannose-Sigma | MAN | 0 |
| Galactose-Sigma | GAL | 0 |
| Xylose-Sigma | XYL | 0 |
| Gluco-Lactone-Fisher | GLT | 0 |
| L+Arabinose-Sigma | LAR | 0 |
| D−Arapinose-Sigma | DAR | 0 |

From the above results, it is clear that dextran and isomaltose are preferred dextranase inducers.

The next step in a most preferred embodiment of the present invention is to ascertain an optimal point of addition for the inducer. A series of experiments was carried out to determine the optimum inducer addition point.

EXAMPLE 3

Figure 3:
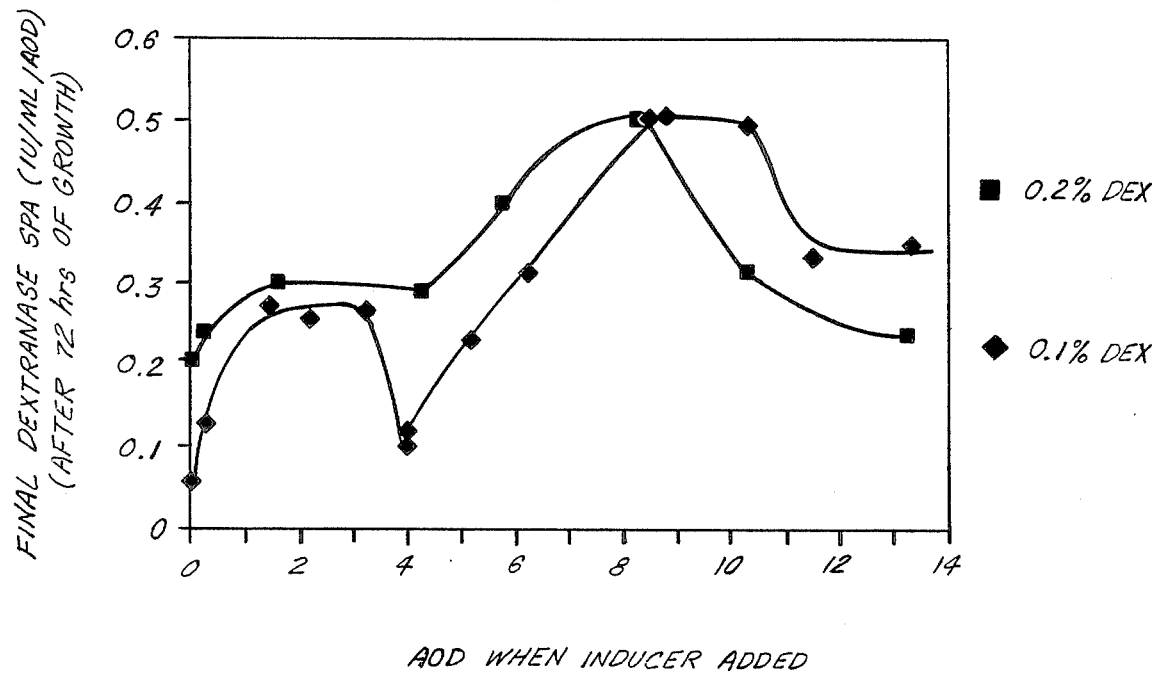
FIG. 3 is a graphical representation of dextranase production induced with 0.1 and 0.2 percent weight/volume dextran cultures on glucose-containing growth media.

An inoculum of Mutant I is cultured on a medium as described hereinabove in Laires et al, supra. The inoculum culture has an optical density of 5.0–6.0 uncorrected at 660 nanometers against a water blank. Then 0.5 ml of this inoculum is added aseptically by a hypodermic syringe to a New Brunswick Microfirm Fermenter containing 500 ml of WW-GLU culture medium. The medium has been previously autoclaved in the fermenter vessel for 15 minutes at 121° C. and 15 psi. After cooling to 27° C., 0.5 ml of sterile trace metal solution is added. The pH control is maintained by using a 3.0 molar NaOH controlled drip as measured by an Ingold type pH electrode which was UV sterilized before being aseptically inserted into the vessel. Temperature is controlled by an external thermal regulator which monitors the temperature of the vessel and is capable of heating on demand. Cooling is accomplished by use of a coldfinger attached to an external refrigeration unit. A pyrex gas dispersion tube allows for uniform aeration. Agitation is accomplished with the use of a magnetic stirrer inside of the vessel controlled externally with a Fisher Versamix stir plate. Sampling is accomplished by retrieving 15 ml aliquots from a sampling port at various time intervals. Time zero is designated as the initial injection of the inoculum into the vessel. The standard operating conditions for the fermentation experiments are stirring rate of 200 rpm, aeration rate of 0.5 liters per minute of air, pH controlled with 3.0 molar sodium hydroxide, temperature of 27° C., volume 500 ml of WW-GLU medium and 0.5 ml of the inoculum. At various points during the fermenter runs, either of two different concentrations of inducer was added. The composite result of dextranase production is given as the enzyme specific activity in IU/ml/AOD as shown in FIG. 3. The curves generated, for both 0.1 and 0.2 percent by weight of dextran per unit volume, show clearly that inducer addition at an adjusted optical density of between 8.0 and 10.0 provides the greatest dextranase specific activity. Further, because there is no concentration effect between the high point at the two concentrations, a lower amount of dextran could probably be used without decreasing dextranase specific activity.

The dextranase produced according to the invention can be easily formulated into toothpaste or tooth powder, rubbing ointment or lotion, mouthwash, chewing gum, food, beverages and the like. Additionally, the dextranase product produced in accordance with this invention is capable of hydrolyzing dextran to give useful products such as monosaccharide glucose, the disaccharide isomaltose and higher oligosaccharides.

It is clear that additional mutations or variants of the foregoing species could be found which have high hyperproductivity or different inducer substrates and optima; however, such changes must be considered in the light of the foregoing disclosure. In view of this, it is clear from the above description that skilled practitioners will recognize modifications or changes which can be made without departing from the scope or spirit of the present invention. Therefore it is desired that the invention be limited only by the lawful scope of the following claims.

We claim:

1. A culture of the strain of *Lypomyces starkeyi*, ATCC No. 20825, having the capability to hyperproduce extracellular dextranase about three times the dextranase production of the wild variety after 72 hours when cultured at a controlled pH in the range of from about 3.0 to about 4.0 in an aqueous nutrient medium containing assimilable carbon source, nitrogen source, and mineral source.

2. An improved method for producing an extracellular dextranase which comprises culturing a mutant strain of a yeast of the genus Lypomyces produced by ultraviolet light, irradiation of the parent strain *Lypomyces starkeyi*, ATCC No. 12659, which mutant is identified as ATCC No. 20825 and characterized by hyperproduction of dextranase of about three times the dextranase production of the wild variety after 72 hours at a controlled pH in the range of about 3.0 to 4.0 in the presence of an aqueous nutrient medium containing an assimilable carbon source.

3. A process for optimizing production of extracellular dextranase which process comprises culturing a strain of the yeast *Lypomyces starkeyi*, ATCC No. 20825 having the capability to hyperproduce dextranase at about three times the dextranase production of the wild variety after about 72 hours at a controlled pH in the range of about 3.0 to about 4.0, using a non-dextran, assimilable carbon source and adding a dextran inducer at a stage of growth identified as having an adjusted optical density of from about 8.0 to about 10.0 at 660 nm compared with water.

4. The culture of claim 1 in which the assimilable carbon source is selcted from dextran, glucose, or mixtures thereof.

5. The culture of claim 4 in which the assimilable carbon source is dextran.

6. The culture of claim 4 in which the assimilable carbon source is glucose.

7. The culture of claim 4 in which the assimilable carbon source is a mixture of dextran and glucose.

8. The method of claim 2 in which the vegetative cells are separated to produce a dextranase-containing culture supernate.

9. The method of claim 2 in which the assimilable carbon source is selected from dextran, glucose, or mixtures thereof.

10. The method of claim 9 in which the assimilable carbon source is dextran.

11. The method of claim 9 in which the assimilable carbon source is glucose.

12. The method of claim 9 in which the assimilable carbon source is a mixture of dextran and glucose.

13. The process of claim 3 in which said dextran inducer is added in an amount of from 0.05 to about 0.2 percent by weight per unit volume of the culture medium.

14. The process of claim 3 in which said non-dextran, assimilable carbon source is selected from glucose, fructose and sucrose.

15. The process of claim 14 in which said non-dextran, assimilable carbon source is glucose.

16. The process of claim 15 in which said dextran inducer is added to said culture medium at an adjusted optical density of about 8.0 to 8.5.

17. The process of claim 3 in which said non-dextran, assimilable carbon source which is a carbohydrate-containing material selected from corn steep liquor and molasses.

* * * * *